United States Patent [19]

Seymour

[11] Patent Number: 5,377,824
[45] Date of Patent: Jan. 3, 1995

[54] DEVICE FOR STORING TOOTHBRUSHES

[76] Inventor: Clyde O. Seymour, P.O. Box 286, Medicine Bow, Wyo. 82329

[21] Appl. No.: 160,216

[22] Filed: Dec. 2, 1993

[51] Int. Cl.⁶ .................. B65D 81/24; B65D 51/18; A47B 73/00; A61L 2/18
[52] U.S. Cl. ..................... 206/209.1; 206/362.1; 211/75; 220/253; 422/300
[58] Field of Search ............ 206/209.1, 15.2, 15.3, 206/362.1, 362.2, 362.3; 220/253, 256, 336; 422/300, 28; 211/75

[56] References Cited

U.S. PATENT DOCUMENTS

| | | | |
|---|---|---|---|
| 311,415 | 1/1885 | Cleveland | 220/253 X |
| 1,507,466 | 9/1924 | Collins | 206/209.1 |
| 3,169,679 | 2/1965 | Hunter | 220/336 X |
| 3,727,748 | 4/1973 | Brown | 206/362.1 |
| 3,750,890 | 8/1973 | Smith et al. | 211/75 |
| 4,915,219 | 4/1990 | Ohimo | 206/209.1 |
| 4,991,737 | 2/1991 | Edelman | 220/253 X |
| 4,997,629 | 3/1991 | Marchand et al. | 422/300 |
| 5,086,916 | 2/1992 | Gray | 206/209.1 |
| 5,107,987 | 4/1992 | Palazzolo et al. | 206/209.1 |

*Primary Examiner*—Bryon P. Gehman

[57] ABSTRACT

A container for the storage of toothbrushes in an antiseptic liquid comprising: a container having a circular bottom wall, an annular upper opening, and a side wall therebetween, the side wall having an annular lower extent and an annular upper extent and a curved intermediate extent therebetween, the upper extent terminating in external threads; a cap having an upper circular surface and downwardly extending side walls in an annular configuration with internal threads matable with the external threads of the container; a plurality of apertures formed in a circular surface of the cap of a sufficient size to receive and allow passage of the bristle end of a toothbrush therethrough; a handle in a cylindrical configuration extending upwardly from the center of the cap between the apertures; and a rotatable cover positionable over the cap, the cover having a circular surface and downwardly extending side walls terminating in inwardly directed flanges received in a first annular recess formed in the cap and a second annular recess formed in the cover for receiving the handle of the cap.

2 Claims, 4 Drawing Sheets

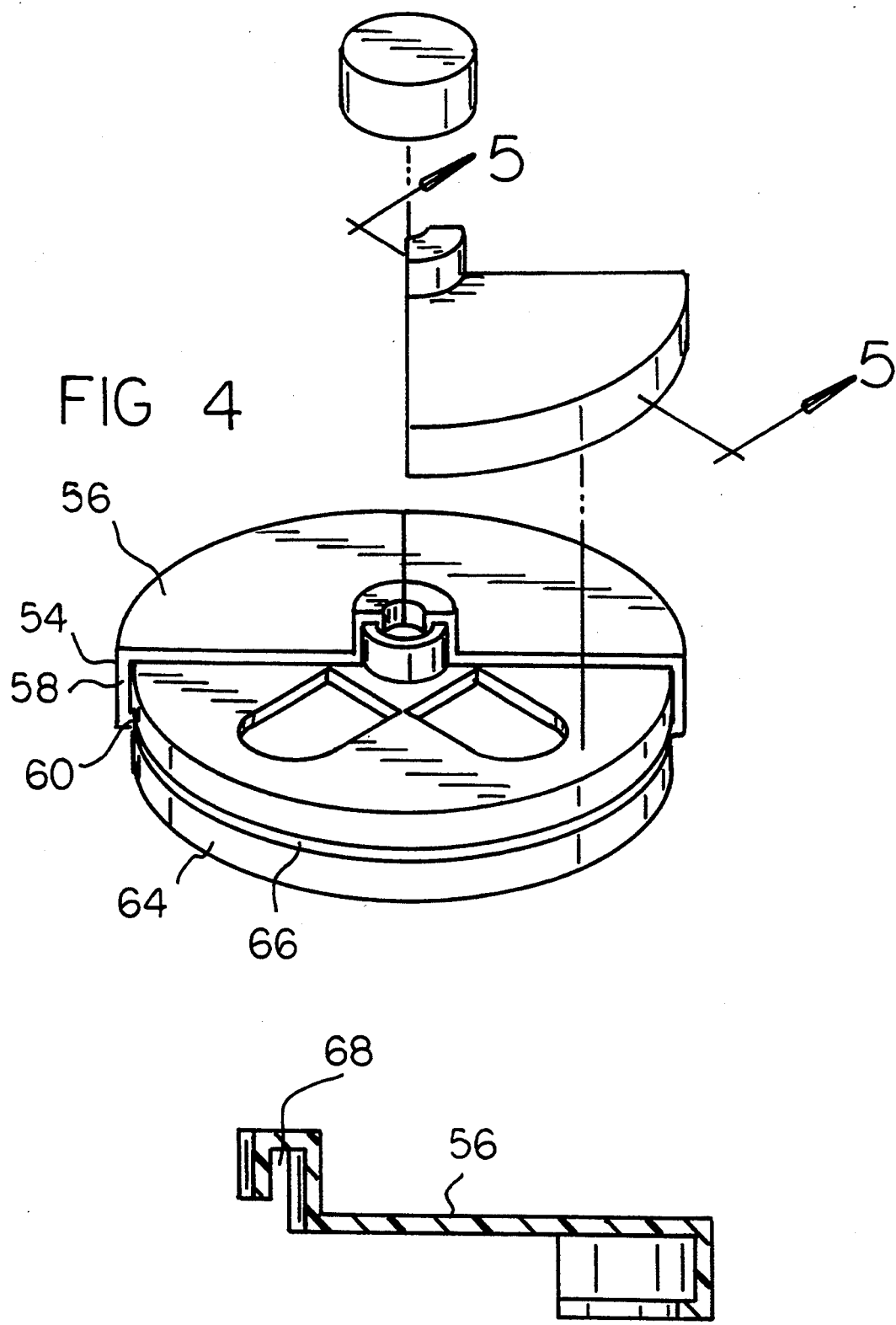

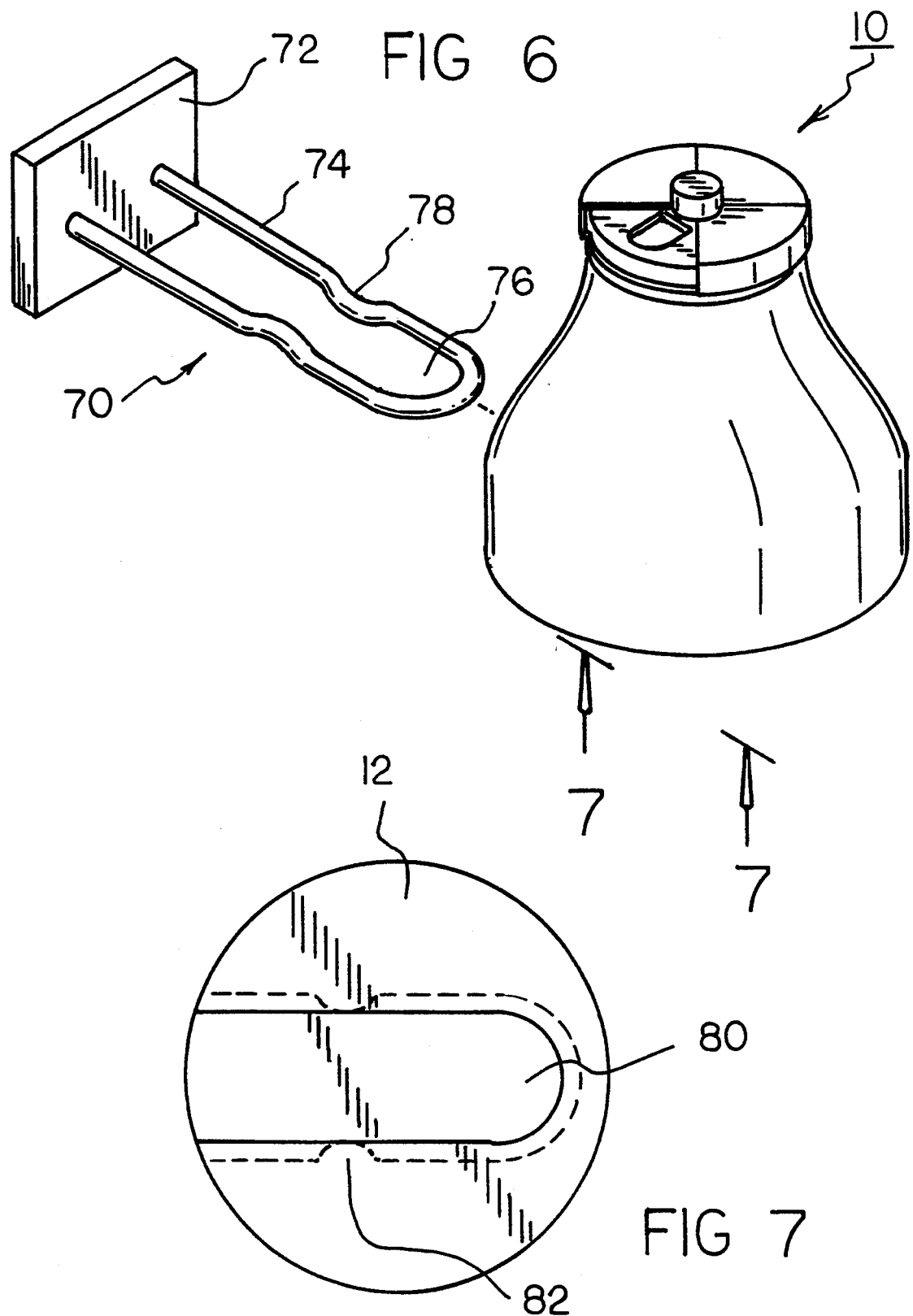

DEVICE FOR STORING TOOTHBRUSHES

BACKGROUND OF THE INVENTION

1. Field of the Invention

The present invention relates to storage devices and more particularly pertains to storage devices which may be used for storing toothbrushes.

2. Description of the Prior Art

The use of devices for storing toothbrushes is known in the prior art. More specifically, devices for storing toothbrushes heretofore devised and utilized for sanitation purposes are known to consist basically of familiar, expected and obvious structural configurations, notwithstanding the myriad of designs encompassed by the crowded prior art which have been developed for the fulfillment of countless objectives and requirements.

The prior art discloses a large number of devices for storing toothbrushes. By way of example, U.S. Pat. No. 4,997,629 to Marchand discloses a container for toothbrushes wherein the toothbrushes are stored bristles up.

U.S. Pat. No. 4,214,657 to Winston discloses a container for toothbrushes wherein the toothbrushes are stored either bristles up or bristles down.

U.S. Pat. Nos. 4,915,219 to Ottimo; 5,086,916 to Gray and 5,107,987 to Palazzolo disclose various configurations of containers for toothbrushes wherein the toothbrushes are stored bristles down in a fluid.

In this respect, the device for storing toothbrushes according to the present invention substantially departs from the conventional concepts and designs of the prior art, and in so doing provides an apparatus primarily developed for the purpose of storing toothbrushes in an antiseptic liquid.

Therefore, it can be appreciated that there exists a continuing need for new and improved devices for storing toothbrushes. In this regard, the present invention substantially fulfills this need.

SUMMARY OF THE INVENTION

In view of the foregoing disadvantages inherent in the known types of devices for storing toothbrushes now present in the prior art, the present invention provides improved devices for storing toothbrushes construction wherein the same can be utilized for storing toothbrushes in an antiseptic fluid. As such, the general purpose of the present invention, which will be described subsequently in greater detail, is to provide new and improved devices for storing toothbrushes apparatus and method which have all the advantages of the prior art and none of the disadvantages.

To attain this, the present invention essentially comprises a container for the storage of toothbrushes in an antiseptic liquid comprising, in combination a container having a circular bottom wall, an annular upper opening, and a side wall therebetween, the side wall having an annular lower extent and an annular upper extent and a curved intermediate extent therebetween, the upper extent terminating in external threads; a quantity of antiseptic fluid located within the container; a cap having an upper circular surface and downwardly extending side walls in an annular configuration with internal threads matable with the external threads of the container; a plurality of apertures formed in the circular surface of the cap of a sufficient size to receive and allow passage of the bristle end of a toothbrush therethrough; a handle in a cylindrical configuration extending upwardly from the center of the cap between the apertures; and a rotatable cover positionable over the cap, the cover having a circular upper surface and downwardly extending sidewalls terminating in inwardly directed flanges received in annular recesses formed in the cap and an annular recess formed in the lower surface of the cover for receiving the handle of the cap;

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is a further object of the present invention to provide new and improved devices for storing toothbrushes which is of a durable and reliable construction.

An even further object of the present invention is to provide new and improved devices for storing toothbrushes which is susceptible of a low cost of manufacture with regard to both materials and labor, and which accordingly is then susceptible of low prices of sale to the consuming public, thereby making such devices for storing toothbrushes economically available to the buying public.

Still yet another object of the present invention is to provide new and improved devices for storing toothbrushes which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an exploded perspective view of the cap of the device for storing toothbrushes constructed in accordance with an alternate embodiment of the invention.

FIG. 5 is a sectional view of the cap of the device for storing toothbrushes of the prior Figure taken along line 5—5 of FIG. 4.

FIG. 6 is a perspective view of a device for storing toothbrushes constructed in accordance with another alternate embodiment of the invention.

FIG. 7 is a sectional view of the device for storing toothbrushes of the prior Figure taken along line 7—7 of FIG. 6.

DESCRIPTION OF THE PREFERRED EMBODIMENTS

Figure 1:
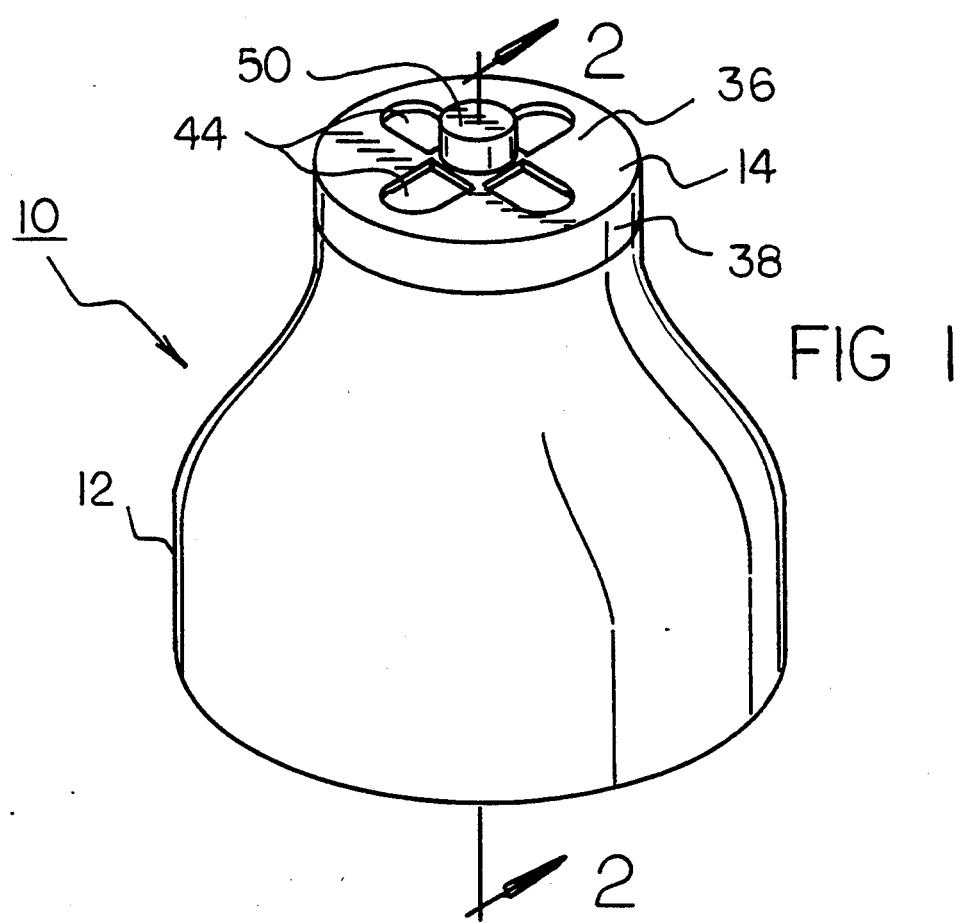
FIG. 1 is a perspective view of the device for storing toothbrushes.
Figure 2:
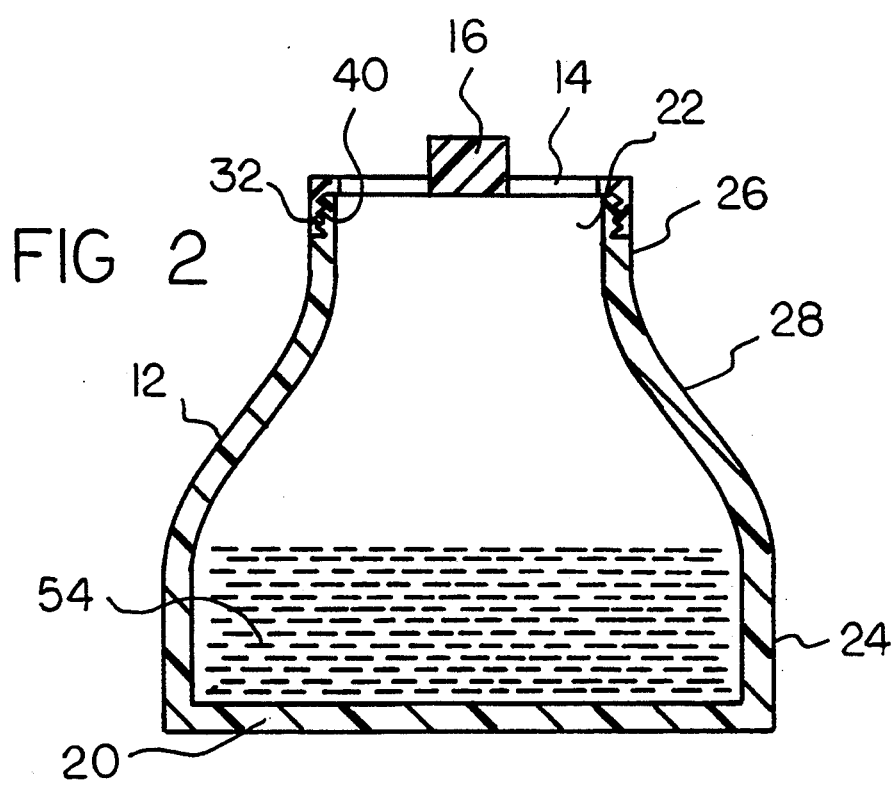
FIG. 2 is a sectional view of the device for storing toothbrushes of the prior Figure taken along line 2—2 of FIG. 1.
Figure 3:
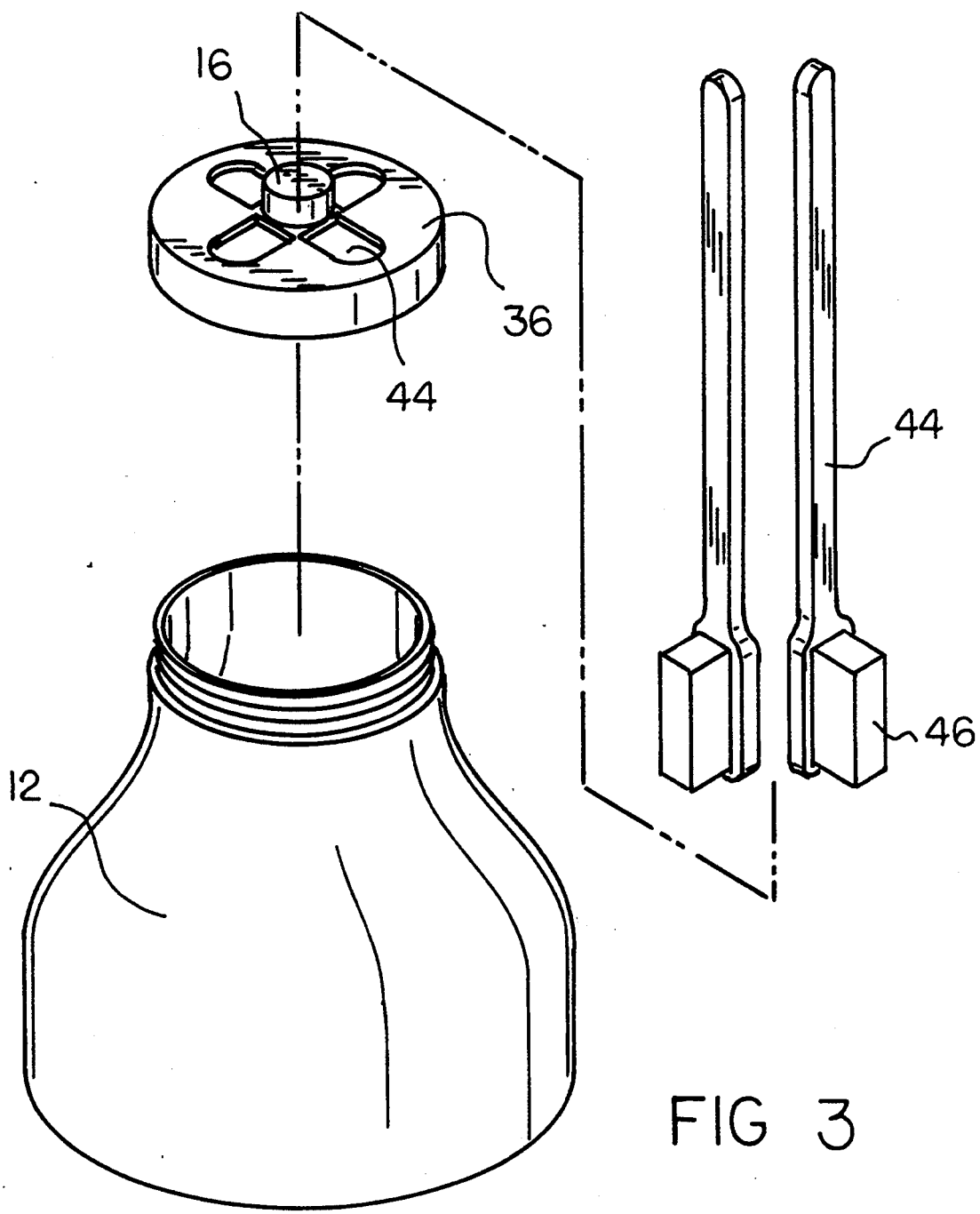
FIG. 3 is an exploded perspective view of the device for storing toothbrushes of the prior Figures.

With reference now to the drawings, and in particular to FIG. 1 thereof, new and improved devices for storing toothbrushes embodying the principles and concepts of the present invention and generally designated by the reference numeral 10 will be described.

The container of the subject invention is adapted for the storage of toothbrushes. The preferred storage is in a quantity of an antiseptic liquid within the container for the storage. With an overview standpoint the invention includes the container 12, the cap 14 to close the top of the container and a handle 16 mounted on the cap. In addition, as an option, the container 10 include a rotatable cover as well as a wall mounted holder.

With regard to the container 10, such is constructed to have a circular bottom wall 20. The bottom wall is at the lower end of the container. At the upper end is an annular opening 22. Between the annular opening at the top of the container and the circular bottom wall is a side wall coupling the upper and lower ends. The side wall is formed with an annular lower extent 24 and an annular upper extent 26 between the upper and lower extends is a curved intermediate extent 28 coupling the upper and lower extends. Note is taken that the exterior surface of the annular upper extent is provided with threads 32.

Mountable on top of the upper extent 26 of the container 10 is a cap 14. The cap as an upper circular surface 36. At the periphery of the upper circular surface are downwardly extending side walls 38 in an annular configuration. The interior surface of the annular side walls are formed with threads 40. The threads 40 cooperate with the threads 32 of the container for coupling the cap to the container.

Formed within the upper circular surface of the cap are a plurality of apertures 44 in the preferred embodiment as disclosed, four such apertures are equally positioned 90 degrees from each other. It should be understood that for other applications different numbers of apertures could be utilized as a function of the number of toothbrushes intended to be maintained within the container. The apertures are of sufficient size as to allow the passage of the end of a toothbrush 44 and with its bristles 46.

In addition to the apertures, the cap is provided with a handle 50. The handle is cylindrical in cross section and of a sufficient size to be grasped by a user. Its central axis is coextensive with the axis of the cap and of the container. In this manner, the cap may be removed from the container by grasping the handle and rotating it in the appropriate direction. The handle extends upward from the center of the cap centrally spaced between the apertures.

The last component of the container is the fluid 54. The fluid is an antiseptic liquid positionable in the container to adapt sufficiently to completely cover the bristle end 46 of the toothbrush 44 when in use. In this manner, a toothbrush when not in use will be maintain in a antiseptic condition. The scent thereof will be pleasant and the taste when brushing teeth with such toothbrush will be improved.

Shown in FIGS. 4 and 5 is an alternative embodiment of the invention. In accordance with the alternate embodiment, a rotatable cover 54 is employed. The cover is circular in its major extent. The cover 54 has downwardly extending side walls 58 at its periphery. The lower ends of the side walls turn inwardly with projections 60. In this embodiment, the cap 64 is provided with an annular recess 66 for receiving the internal projection 60 of the side walls 58. Further, the cover has an annular recess 68 formed in the lower surface thereof for receiving the handle of the cap. This maintains that the rotatable in position over the cap. In this embodiment, the cover is shown as covering two of the four holes. This leaves available for use the two uncovered holes.

The last embodiment of the invention involves the use of a bracket 70. The bracket 70 includes a wall mounted plate 72 and a flexible spring member 74 having its free ends attached to the plate 72. The end of member 74 remote from the plate 72 is in a U-shaped configuration with an enlargement 76. The container 12 has a member receiving slot 80 formed in the lower surface thereof. The slot has a narrowed portion 82 formed therein for receiving and engaging the restricted area 78. In use, the lower end of the container 12 is positioned such that the spring member is slidably positioned within the receiving slot until the narrowed portion of the container engages the restricted area of the spring member. In this manner, the container will be conventionally supported at an appropriate height for use as a function of where the user wishes to mount plate 72 on a wall.

More specifically, it will be noted that the toothbrush is one grooming item that no one can do without. Whether traveling or at home, good dental hygiene is an important part of daily life. But brushing one's teeth requires a toothbrush that is clean and in good condition. When most people finish brushing, they simply rinse their toothbrush and place it back in its holder where hair spray, dust and germs can deposit on it. Clearly, what is needed is a toothbrush holder that can be filled with an antiseptic capable of keeping the toothbrush as clean as possible. The present invention is a new toothbrush holder that employs a reusable and refillable antiseptic liquid for keeping a plurality of toothbrushes clean.

The present invention is fabricated from plastic in a variety of colors. It is molded in a shape very similar to an inverted parabola, with a wide stable base, and a small neck that resists spilling the antiseptic. The neck is enclosed by a screw top that has four openings for inserting the brushes. To use the present invention, it is first filled with the antiseptic. Then the top is installed. The bristles can then be inserted through the screw top until they rest completely submerged on the bottom. Each time a brush is removed, it is clean, pre-wetted, and fresh tasting.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A container for the storage of toothbrushes in an antiseptic liquid comprising, in combination:

a container having a circular bottom wall, an annular upper opening, and a side wall therebetween, the side wall having an annular lower extent and an annular upper extent and curved intermediate extent therebetween, the upper extent terminating in external threads;

a quantity of antiseptic fluid located within the container;

a cap having an upper circular surface and downwardly extending side walls in an annular configuration with internal threads matable with the external threads of the container;

a plurality of apertures formed in the circular surface of the cap of a sufficient size to receive and allow passage of the bristle end of a toothbrush therethrough;

a handle in a cylindrical configuration extending upwardly from the center of the cap between the apertures; and a rotatable cover positionable over the cap, the cover having a circular upper surface and downwardly extending side walls terminating in inwardly directed flanges received in a first annular recess formed in the cap and a second annular recess formed in the cover for receiving the handle of the cap.

2. A container for the storage of toothbrushes in an antiseptic liquid comprising:

a container having a circular bottom wall, an annular upper opening, and a side wall therebetween, the side wall having an annular lower extent and an annular upper extent and a curved intermediate extent therebetween, the upper extent terminating in external threads the circular bottom wall further including a slot therein;

a cap having an upper circular surface and downwardly extending side walls in an annular configuration with internal threads matable with the external threads of the container;

a plurality of apertures formed in the circular surface of the cap of a sufficient size to receive and allow passage of the bristle end of a toothbrush therethrough;

a handle in a cylindrical configuration extending upwardly from the center of the cap between the apertures;

a rotatable cover positionable over the cap, the cover having a circular upper surface and downwardly extending side walls terminating in inwardly directed flanges received in a first annular recess formed in the cap and a second annular recess formed in the cover for receiving the handle of the cap; and a wall-mounted holder with a U-shaped flexible spring member adapted to be received in the slot formed in the bottom wall of the container.

* * * * *